(12) United States Patent  
Burk

(10) Patent No.: US 7,915,316 B2
(45) Date of Patent: Mar. 29, 2011

(54) SULFONAMIDES

(75) Inventor: Robert M. Burk, Laguna Beach, CA (US)

(73) Assignee: Allergan, Inc, Irvine, CA (US)

( * ) Notice: Subject to any disclaimer, the term of this patent is extended or adjusted under 35 U.S.C. 154(b) by 0 days.

(21) Appl. No.: 11/465,847

(22) Filed: Aug. 21, 2006

(65) Prior Publication Data

US 2007/0142471 A1 Jun. 21, 2007

Related U.S. Application Data

(60) Provisional application No. 60/710,537, filed on Aug. 22, 2005.

(51) Int. Cl.
*A01N 41/06* (2006.01)
*A01N 41/02* (2006.01)

(52) U.S. Cl. .......... 514/601; 514/600; 514/91; 514/183; 514/562; 514/579; 514/95; 562/430

(58) Field of Classification Search ....................... None
See application file for complete search history.

(56) References Cited

U.S. PATENT DOCUMENTS

| | | | | |
|---|---|---|---|---|
| 4,456,616 | A | * | 6/1984 | YHaslanger et al. .......... 514/469 |
| 5,025,025 | A | * | 6/1991 | Bhagwat et al. .............. 514/340 |
| 5,834,498 | A | * | 11/1998 | Burk ............... 514/445 |
| 5,877,211 | A | | 3/1999 | Woodward |
| 7,034,043 | B2 | * | 4/2006 | Scott et al. ..................... 514/330 |
| 2003/0166631 | A1 | * | 9/2003 | Dumont et al. .......... 514/211.01 |
| 2005/0065133 | A1 | * | 3/2005 | Lee et al. ........................ 514/167 |
| 2005/0203086 | A1 | * | 9/2005 | Constan et al. ............. 514/227.5 |
| 2006/0135773 | A1 | * | 6/2006 | Semple et al. .................. 546/22 |
| 2006/0217433 | A1 | * | 9/2006 | Conner et al. ................ 514/418 |

FOREIGN PATENT DOCUMENTS

| | | | |
|---|---|---|---|
| EP | 1000619 | | 5/2000 |
| WO | WO98/28264 | | 7/1998 |
| WO | WO99/19300 | | 4/1999 |
| WO | WO 02/39987 | * | 5/2002 |
| WO | WO2004/078169 | | 9/2004 |

OTHER PUBLICATIONS

Silverman B. R., The organic Chemistry of Drug Design and Drug Action, 1992, Academic Press, Inc., (7 pages).*
Cioffi and Van Buskirk [*Surv. of Ophthalmol.*, 38, Suppl. p. S107-16, discussion S116-17, May 1994] in the article, "Microvasculature of the Anterior Optic Nerve".
Matusi published a paper on the "Ophthalmologic aspects of Systemic Vasculitis" [*Nippon Rinsho*, 52 (8), p. 2158-63, Aug. 1994].
B. Schwartz, in "Circulatory Defects of the Optic Disk and Retina in Ocular Hypertension and High Pressure Open-Angle Glaucoma" [*Surv. Ophthalmol.*, 38, Suppl. pp. S23-24, May 1994].
Starr, M.S. *Exp. Eye Res.* 1971, 11, pp. 170-177; Bito, L. Z. *Biological Protection with Prostaglandins* Cohen, M. M., ed., Boca Raton, Fla, CRC Press Inc., 1985, pp. 231-252.
Bito, L. Z., *Applied Pharmacology in the Medical Treatment of Glaucomas* Drance, S. M. and Neufeld, A. H. eds., New York, Grune & Stratton, 1984, pp. 477-505).
Jones et al, Journal of Medicinal Chemistry, 1977, vol. 20, No. 10, pp. 1299-1304.

* cited by examiner

*Primary Examiner* — Porfirio Nazario Gonzalez
*Assistant Examiner* — Yate K Cutliff
(74) *Attorney, Agent, or Firm* — Doina G. Ene; John E. Wurst; Kevin J. Forrestal

(57) ABSTRACT

The present invention provides
R, $R^1$, $R^2$, $R^3$, X, c, d, e, f, g, x, y, a, b, z and n are defined in the specification.
These compounds are useful in lowering IOP and/or treating glaucoma or providing neuroprotection to the eye of a human patient.

4 Claims, 2 Drawing Sheets

Scheme 3

Scheme 3

SULFONAMIDES

CROSS REFERENCE TO RELATED APPLICATIONS

This application is based on, and claims the benefit of, U.S. Provisional Application No. 60/710,537, filed Aug. 22, 2005, and which is incorporated herein by reference.

BACKGROUND OF THE INVENTION

1. Field of the Invention

The present invention relates to novel sulfonamides which are useful in lowering intraocular pressure and/or glaucoma. These compounds also provide neuroprotection to the eye of a human.

2. Description of the Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical α-adrenoreceptor antagonists have traditionally been the drugs of choice for treating glaucoma.

It has long been know that one of the sequelae of glaucoma is damage to the optic nerve head. This damage, referred to as "cupping", results in depressions in areas of the nerve fiber of the optic disk. Loss of sight from this cupping is progressive and can lead to blindness if the condition is not treated effectively.

Unfortunately lowering intraocular pressure by administration of drugs or by surgery to facilitate outflow of the aqueous humor is not always effective in obviating damage to the nerves in glaucomatous conditions. This apparent contradiction is addressed by Cioffi and Van Buskirk [*Surv. of Ophthalmol.*, 38, Suppl. p. S107-16, discussion S116-17, May 1994] in the article, "Microvasculature of the Anterior Optic Nerve". The abstract states:

The traditional definition of glaucoma as a disorder of increased intraocular pressure (IOP) oversimplifies the clinical situation. Some glaucoma patients never have higher than normal IOP and others continue to develop optic nerve damage despite maximal lowering of IOP. Another possible factor in the etiology of glaucoma may be regulation of the regional microvasculature of the anterior optic nerve. One reason to believe that microvascular factors are important is that many microvascular diseases are associated with glaucomatous optic neuropathy.

Subsequent to Cioffi, et al., Matusi published a paper on the "Ophthalmologic aspects of Systemic Vasculitis" [*Nippon Rinsho*, 52 (8), p. 2158-63, August 1994] and added further support to the assertion that many microvascular diseases are associated with glaucomatous optic neuropathy. The summary states:

Ocular findings of systemic vasculitis, such as polyarteritis nodosa, giant cell angitis and aortitis syndrome were reviewed. Systemic lupus erythematosus is not categorized as systemic vasculitis, however its ocular findings are microangiopathic. Therefore, review of its ocular findings was included in this paper. The most common fundus finding in these diseases is ischemic optic neuropathy or retinal vascular occlusions. Therefore several points in diagnosis or pathogenesis of optic neuropathy and retinal and choroidal vaso-occlusion were discussed. Choroidal ischemia has come to be able to be diagnosed clinically, since fluorescein angiography was applied in these lesions. When choroidal arteries are occluded, overlying retinal pigment epithelium is damaged. This causes disruption of barrier function of the epithelium and allows fluid from choroidal vasculatures to pass into subsensory retinal spaces. This is a pathogenesis of serous detachment of the retina. The retinal arterial occlusion formed non-perfused retina. Such hypoxic retina released angiogenesis factors which stimulate retinal and iris neovascularizations and iris neovascularizations may cause neovascular glaucoma.

B. Schwartz, in "Circulatory Defects of the Optic Disk and Retina in Ocular Hypertension and High Pressure Open-Angle Glaucoma" [*Surv. Ophthalmol.*, 38, Suppl. pp. S23-24, May 1994] discusses the measurement of progressive defects in the optic nerve and retina associated with the progression of glaucoma. He states:

Fluorescein defects are significantly correlated with visual field loss and retinal nerve fiber layer loss. The second circulatory defect is a decrease of flow of fluorescein in the retinal vessels, especially the retinal veins, so that the greater the age, diastolic blood pressure, ocular pressure and visual field loss, the less the flow. Both the optic disk and retinal circulation defects occur in untreated ocular hypertensive eyes. These observations indicate that circulatory defects in the optic disk and retina occur in ocular hypertension and open-angle glaucoma and increase with the progression of the disease.

Thus, it is evident that there is an unmet need for agents that have neuroprotective effects in the eye that can stop or retard the progressive damage that occurs to the nerves as a result of glaucoma or other ocular afflictions.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M. S. *Exp. Eye Res.* 1971, 11, pp. 170-177; Bito, L. Z. *Biological Protection with Prostaglandins* Cohen, M. M., ed., Boca Raton, Fla., CRC Press Inc., 1985, pp. 231-252; and Bito, L. Z., *Applied Pharmacology in the Medical Treatment of Glaucomas* Drance, S. M. and Neufeld, A. H. eds., New York, Grune & Stratton, 1984, pp. 477-505). Such prostaglandins include $PGF_{2\alpha}$, $PGF_{1\alpha}$, $PGE_2$, and certain lipid-soluble esters, such as $C_1$ to $C_5$ alkyl esters, e.g. 1-isopropyl ester, of such compounds.

BRIEF SUMMARY OF THE INVENTION

The present invention provides novel compounds, having the formula wherein the dotted line indicates the presence or absence of a bond;
R is selected from the group consisting of halo, $C_1$-$C_{10}$ alkyl, $C_1$-$C_{10}$ alkoxy, hydroxy and $NR^4R^5$;
$R^1$ is selected from the group consisting of $C_1$-$C_{10}$ alkoxy, OH and $NR^4R^5$;
$R^2$ is selected from the group consisting of $C_1$-$C_{10}$ alkyl, heteroaryl, carbocyclic aryl, e.g. phenyl, and $(CH_2)_nOH$;
$R^3$ is selected from the group consisting of $C_1$-$C_{10}$ alkyl, heteroaryl, carbocyclic aryl, e.g. phenyl, mono, -di-, tri-substituted carbocyclic aryl, e.g. phenyl and heteroaryl;
$R^4$ and $R^5$ are independently selected from the group consisting of H, $C_1$-$C_{10}$ alkyl, $C_1$-$C_{10}$ alkyl hydroxyl;
X is OH or CO;
c is 0 or 1;
d is 0 or 1, and when c is 0, d is 1 and when d is 0, c is 1;
e is 0 or 1, and when d is 1, e is 0;
f is 0 or 1;
g is 1 or 2;
x is 0 or 1;
y is 0 or 1, and when y is 1, x is 1;
a is 0 or 1 or 2;
b is 0 or 1, provided however when X is CO, a is 0;
z is 0, 1, 2 or 3; and
n is 0 or 1.

The present compounds are useful in lowering intraocular pressure and/or glaucoma. These compounds also provide neuroprotection to the eye of a human.

DETAILED DESCRIPTION OF THE INVENTION

Figure 1:
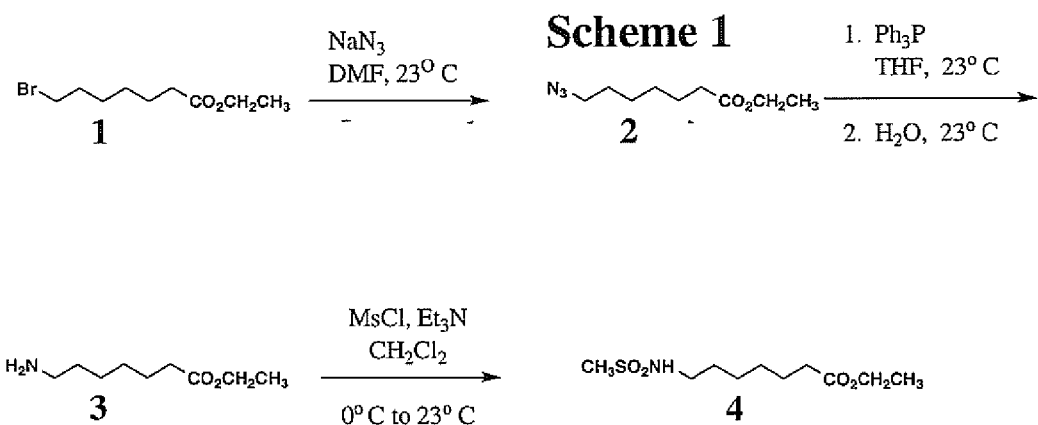
FIG. 1 describes a general synthetic scheme to show the preparation of an intermediate which for the preparation of the compounds of this invention.
Figure 1:
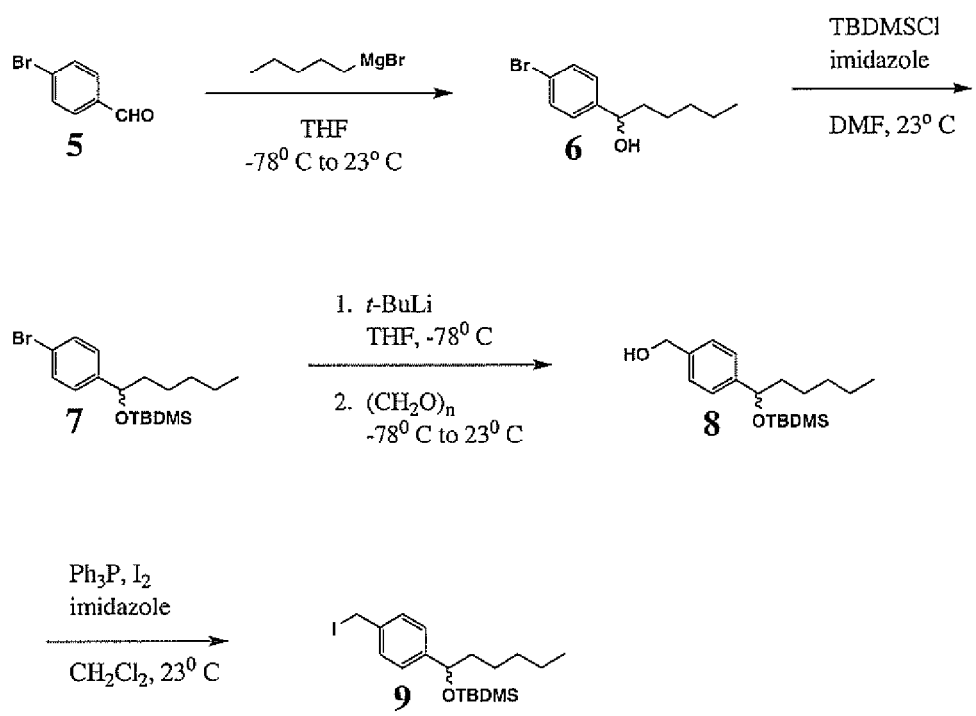

The novel compounds of the present invention have the general formula I wherein the dotted line indicates the presence or absence of a bond;
R is selected from the group consisting of halo, $C_1$-$C_{10}$ alkyl, $C_1$-$C_{10}$ alkoxy, hydroxy and $NR^4R^5$;
$R^1$ is selected from the group consisting of $C_1$-$C_{10}$ alkoxy, OH and $NR^4R^5$;
$R^2$ is selected from the group consisting of $C_1$-$C_{10}$ alkyl, heteroaryl, carbocyclic aryl, e.g. phenyl, and $(CH_2)_nOH$;
$R^3$ is selected from the group consisting of $C_1$-$C_{10}$ alkyl, heteroaryl, carbocyclic aryl, e.g. phenyl, mono, -di-, tri-substituted carbocyclic aryl, e.g. phenyl and heteroaryl;
$R^4$ and $R^5$ are independently selected from the group consisting of H, $C_1$-$C_{10}$ alkyl, $C_1$-$C_{10}$ alkyl hydroxyl;
X is OH or CO;
c is 0 or 1;
d is 0 or 1, and when c is 0, d is 1 and when d is 0, c is 1;
e is 0 or 1, and when d is 1, e is 0;
f is 0 or 1;
g is 1 or 2;
x is 0 or 1;
y is 0 or 1, and when y is 1, x is 1;
a is 0 or 1 or 2;
b is 0 or 1, provided however when X is CO, a is 0;
z is 0, 1, 2 or 3; and
n is 0 or 1.

Heteroaryl includes mono and bicyclic compounds having from 3 to 10 carbon atoms and from 1 to 4 heteroatoms, e.g. N, S, and/or O atoms, in the ring(s). Carbocyclic aryl includes mono and bicyclic compounds having from 6 to 10 carbon atoms in the ring.

In one aspect of this invention, the compounds are represented by general formula II:

In another aspect of the invention, in the novel compounds of formula I, y is 1, z is 2 and R is chloro or y is 0, x is 0, z is 0, n is 0 and $R^3$ is t-butyl.

Preferably $R^1$ is OH or O-lower alkyl or $N(H)_n$(lower alkyl)$_m$ or $N(H)_n$ (lower alkyl hydroxyl)$_m$ wherein n is 0 or 1 and m is 1 or 2. Lower alkyl is defined as a $C_1$ to $C_6$ alkyl.

More preferably $R^1$ is OH or $OCH_3$.

Preferably the n associated with $R^2$ is 1 and $R^2$ is lower alkyl. $R^3$ is preferably selected from the group consisting of phenyl, furanyl and thienyl.

Finally, preferably the benzylic OH group is oriented as an α OH group.

Specific compounds of the invention include:
7-[[4-(1-Hydroxyhexyl)benzyl]methanesulfonylamino]heptanoic acid ethyl ester (11).
7-[[4-(1-Hydroxyhexyl)benzyl]methanesulfonylamino]heptanoic acid (12).
7-[[4-(1-hydroxyhexyl)benzyl]methanesulfonylamino]hept-5-yne-oic acid
7-[[4-(2,6-dichlorophenyloxyethyl)methanesulfonylamino]hept-5-yne-oic acid
7-[[4-(2,6-dichlorophenyloxyethyl)methanesulfonylamino]hept-5-ene-oic acid
7-[[4-(1-t-butyl)benzyl]methanesulfonylamino]heptanoic acid
7-[[4-(1-t-butyl)benzyl]benzenesulfonylamino]heptanoic acid
7-[[4-(1-t-butyl)benzyl]pyridinesulfonylamino]heptanoic acid
7-[[4-(1-t-butyl)benzyl]thiophenelsulfonylamino]heptanoic acid
7-[[4-(1-hydroxyhexyl)benzyl]thiophenesulfonylamino] heptanoic acid 7-[[4-(1-hydroxyhexyl)benzyl]benzenesulfonylamino]heptanoic acid 7-[[4-(1-hydroxyhexyl)benzyl]pyridinesulfonylamino]heptanoic acid 4-[[4-(1-hydroxyhexyl)benzyl]pyridinesulfonylaminomethyl]phenoxyacetic acid 4-[[4-(1-t-butyl)benzyl]pyridinesulfonylaminomethyl]phenoxyacetic acid The compounds of the invention are especially useful in treating ocular hypertension, i.e. lowering elevated intraocular pressure (IOP), and/or glaucoma. These compounds are useful in providing neuroprotection to the eye of a human.

Pharmaceutical compositions including the compounds of this invention may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place of or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-8.0 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations for use in the method of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 μl.

The invention is further illustrated by the following examples which are illustrative of a specific mode of practicing the invention and are not intended as limiting the scope of the claims. (The numbers of the compounds in the Examples correspond to the numbers in the Figures.)

Example 1

7-Azidoheptanoic acid ethyl ester (2)

Sodium azide (1.7 g, 0.026 mol) was added to ethyl 7-bromoheptanoate 1 (4.1 g, 0.017 mol) in DMF (40 mL) at 23° C. The reaction was stirred for 16 h, diluted with pentane and washed with water. The organic portion was washed with brine, dried ($MgSO_4$), filtered and concentrated in vacuo to give 3.22 g (95%) of the azide 2 as a clear, colorless liquid.

Example 2

7-Aminoheptanoic acid ethyl ester (3)

Triphenyphosphine (4.6 g, 17.5 mmol) was added to a solution of the azide (17.0 mmol) in THF (68 mL) at 23° C. After stirring for 16 h $H_2O$ (0.46 mL, 25.5 mmol) was added. The reaction was stirred another 16 h and the solvent was removed in vacuo. The residue was diluted with hexane and the white precipitate was removed by vacuum filtration. The filtrate was concentrated in vacuo to afford the crude amine 3 as a yellow oil.

Example 3

7-Methanesulfonylaminoheptanoic acid ethyl ester (4)

Methanesulfonyl chloride (1.6 mL, 20.0 mmol) was added to a solution of the amine (afforded in the above step) and pyridine (2.1 mL, 25.5 mmol) in $CH_2Cl_2$ (34 mL) at 0° C. The reaction was allowed to warm to room temperature and stirred for an additional 12 h. The reaction solution was diluted with $Et_2O$ and washed with 1 N HCl, saturated aqueous $NaHCO_3$ and brine. The organic portion was dried ($MgSO_4$), filtered and concentrated in vacuo. Flash column chromatography (FCC) (silica gel, 1:1 hex/EtOAc) gave 2.4 g (60%) of the sulfonamide 4 as a white powder.

Example 4

1-(4-Bromophenyl)hexan-1-ol (6)

n-Pentylmagnesium bromide (12.1 mL of a 2.0 M solution in $Et_2O$, 24.0 mmol) was added to a solution of 4-bromobenzaldehyde 5 (4.0 g, 22.0 mmol) at −78° C. The reaction was then warmed to room temperature for 0.5 h and quenched with saturated aqueous $NH_4Cl$. The mixture was extracted with EtOAc and the organic portion was washed with brine, dried ($MgSO_4$), filtered and concentrated in vacuo. FCC (silica gel, 9:1 hex/EtOAc) gave 3.6 g (63%) of the alcohol 6 as a clear, colorless oil.

Example 5

[1-(4-Bromophenyl)hexyloxy]-tert-butyidimethyl silane (7)

t-Butyidimethylsilylchloride (2.49 g, 16.5 mmol) was added to a solution of the alcohol 6 (3.6 g, 14.0 mmol) and imidazole (1.91 g, 28.0 mmol) in DMF (22 mL) at 23° C. The reaction was stirred for 16 h, diluted with $Et_2O$ and washed with 1 N HCl, saturated aqueous $NaHCO_3$ and brine. The organic portion was dried ($MgSO_4$), filtered and concentrated in vacuo. FCC (silica gel, 100% hex) afforded 5.18 g (63%) of the silyl ether 7 as a clear, colorless oil.

Example 6

[4-[1-(tert-butyldimethylsilanyloxy)hexyl]phenyl] methanol (8)

tert-Butyllithium (6.6 mL of a 1.7 M solution in pentane, 11.32 mmol) was added to a solution of the aryl bromide 7 (2.0 g, 5.39 mmol) in THF (22 mL) at −78° C. After 0.5 h paraformaldehyde (323 mg, 8.09 mmol) was added. The reaction was warmed to room temperature and stirred for 16 h. The reaction was quenched with saturated aqueous $NH_4Cl$ and extracted with EtOAc. The organic portion was dried ($MgSO_4$), filtered and concentrated in vacuo. FCC (silica gel, 6:1 hex/EtOAc) yielded 1.2 g (69%) of the alcohol 8 as a clear, colorless oil.

Example 7 tert-Butyl[1-(4-iodomethylphenyl)hexyloxy]dimethylsilane (9)

Iodine (503 mg, 1.98 mmol) was added to a solution of triphenylphosphine (520 mg, 1.98 mmol) and imidazole (169 mg, 2.48 mmol) in $CH_2Cl_2$ (7.0 mL) at 23° C. After 0.5 h a solution of the alcohol (532 mg, 1.65 mmol) in $CH_2Cl_2$ (3.0 mL) was added. The reaction was stirred for 1 h, diluted with hexane and then filtered through celite. The filtrate was concentrated in vacuo and purified by FCC (silica gel, 100% hex) to give 700 mg (98%) of the iodide 9 as a clear, colorless oil.

Example 8

7-[[4-(1-(tert-Butyldimethylsilanyloxy)hexyl)benzyl] methanesulfonylamino]-heptanoic acid ethyl ester (10)

Sodium bis(trimethylsilyl)amide (1.0 mL of a 1.0 M solution in THF, 1.00 mmol) was added to a solution of the sulfonamide 4 (220 mg, 0.88 mmol) in THF (2.2 mL) at 0° C. The reaction was warmed to room temperature and a solution of the iodide 9 (432 mg, 1.00 mmol) in THF (3.0 mL) was added. The reaction was stirred at room temperature for 16 h, quenched with saturated aqueous $NH_4Cl$ and extracted with EtOAc. The organic portion was washed with brine, dried ($MgSO_4$), filtered and concentrated in vacuo. FCC (silica gel, 4:1 hex/EtOAc) gave 159 mg (29%) of the silyl ether 10 as a light yellow viscous oil.

Example 9

7-[[4-(1-Hydroxyhexyl)benzyl]methanesulfonylamino]heptanoic acid ethyl ester (11)

Tetrabutylammonium fluoride (0.6 mL of a 1.0 M solution in THF, 0.6 mmol) was added to a solution of the silylether 10 (159 mg, 0.29 mmol) in THF (3.0 mL) at 23° C. The reaction was stirred for 16 h, diluted with EtOAc and washed with water. The organic portion was washed with brine, dried ($MgSO_4$), filtered and concentrated in vacuo. FCC (silica gel, 2:1 hex/EtOAc) afforded 118.6 mg (94%) of the alcohol 11 as a light yellow, viscous oil.

Example 10

7-[[4-(1-Hydroxyhexyl)benzyl]methanesulfonylamino]heptanoic acid (12)

Lithium hydroxide (0.47 mL of a 0.5 N solution in $H_2O$, 0.236 mmol) was added to a solution of the ester 11 (52 mg, 0.118 mmol) in THF (1.5 mL) at 23° C. The reaction mixture was stirred for 16 h, acidified with 1 N HCl and extracted with EtOAc. The organic portion was washed with brine (2x), dried ($MgSO_4$), filtered and concentrated in vacuo. FCC (silica gel, 100% EtOAc) gave 36.2 mg (72%) of the free acid 12 as a light yellow, viscous oil.

In an in-vitro assay for binding to and activity at various prostaglandin receptors, the compound of Example 10 was shown to be selective at the EP2 and EP4 receptors as compared to the FP, EP1, TP, IP and DP receptors.

The corresponding derivatives of the compound of Example 10, wherein the methane sulfonyl group is replaced by a thiophene sulfonyl, benzene sulfonyl or a pyridine sulfonyl group are also EP2 and EP4 ligands. See Table 1 below.

TABLE 1

| Compound | cAMP | bhEP$_2$ | fhEP$_2$ | bhEP$_4$ | fhEP$_4$ |
|---|---|---|---|---|---|
| 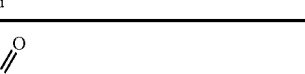 | 16 | 1695 | 406 | 15K | 15K |

TABLE 1-continued

| Compound | cAMP | bhEP$_2$ | fhEP$_2$ | bhEP$_4$ | fhEP$_4$ |
|---|---|---|---|---|---|
| (12) 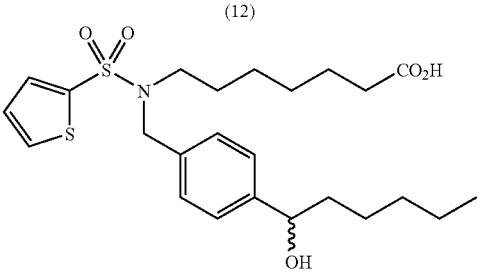 | >10K | 1490 | 600 | 90 | 50K |
| 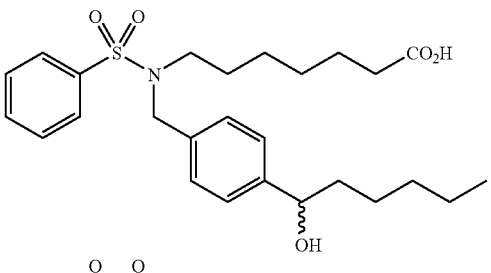 |  | 634 | 150 |  | 50K |
| 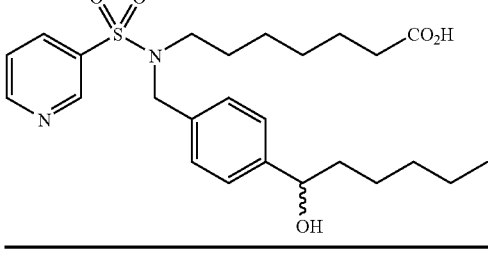 | 138 | 4732 | 275 | 546 | 50K |

Other compounds of the invention wherein the δ phenyl group of the compound of Example 10 is substituted with a t-butyl or two chloro groups or an oxa radical is incorporated into the δ chain or a phenyloxa radical is incorporated in the α chain or the α chain is unsaturated are EP2 ligands as shown in Table 2 below.

Figure 2:
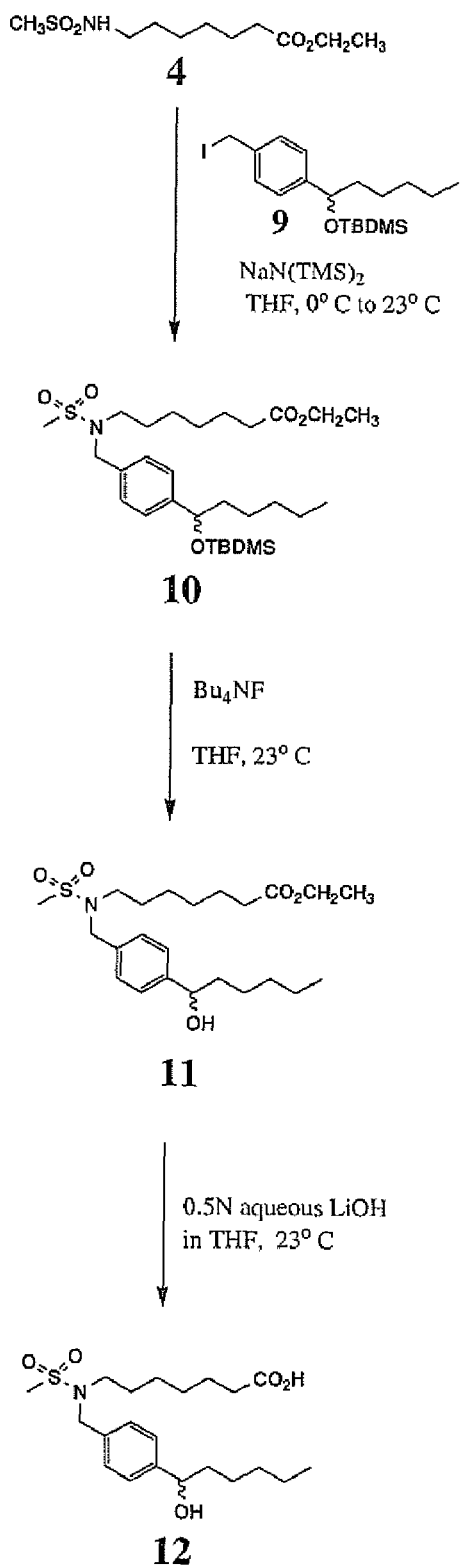
FIG. 2 describes a general synthetic scheme to show the preparation of the compounds of this invention.

These compounds are prepared by substituting the appropriate reactant for reactant 1 of FIG. 1 or reactant 9 of FIGS. 1 and 2 for the designated reactants 1 and 9 of the Examples.

TABLE 2

| Compound | cAMP EC$_{50}$ (nM) | Ca$^{2+}$ signal % PGE$_2$ | EP$_2$ EC$_{50}$ (nM) | Binding % Inh | Ca$^{2+}$ EC$_{50}$ (nM) | Signal % PGE$_2$ | EP$_4$ EC$_{50}$ (nM) | Binding % Inh | Binding EC$_{50}$ (nM) |
|---|---|---|---|---|---|---|---|---|---|
| 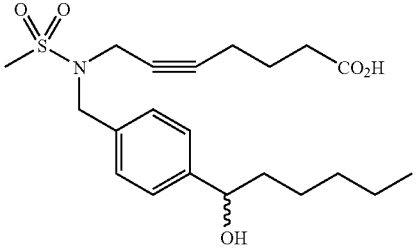 | 24 | 620 | 5675 | NA | | | | | NA |
| | | | NA | NA | NA | | | | 2921 |

TABLE 2-continued

| Compound | cAMP EC$_{50}$ (nM) | Ca$^{2+}$ % PGE$_2$ | signal EC$_{50}$ (nM) | EP$_2$ % Inh | Binding EC$_{50}$ (nM) | Ca$^{2+}$ % PGE$_2$ | Signal EC$_{50}$ (nM) | EP$_4$ % Inh | Binding EC$_{50}$ (nM) | |
|---|---|---|---|---|---|---|---|---|---|---|
| [structure] | 214 | 83 | 2958 | 81 | 1900 | 10 | NA | 64 | 2921 | IP = 403<br>TP = 7008 |
| [structure] | 84 | 90 | 1249 | 87 | 1126 | 5 | NA | 55 | 4166 | IP = 868 |
| [structure] | 156 | 89 | 2313 | 60 | NA | 2 | NA | 41 | NA | IP = 2561 |
| [structure] | 965 | 78 | 964 | 82 | 1540 | 11 | NA | 99 | 373 | |
| [structure] | 126 | 83 | 591 | 73 | 829 | 1 | NA | 71 | 1376 | |
| [structure] | 1968 | 71 | 1132 | 76 | 493 | 9 | NA | 94 | 706 | |

TABLE 2-continued

| Compound | cAMP EC$_{50}$ (nM) | Ca$^{2+}$ % PGE$_2$ | signal EC$_{50}$ (nM) | EP$_2$ % Inh | Binding EC$_{50}$ (nM) | Ca$^{2+}$ % PGE$_2$ | Signal EC$_{50}$ (nM) | EP$_4$ % Inh | Binding EC$_{50}$ (nM) | |
|---|---|---|---|---|---|---|---|---|---|---|
| 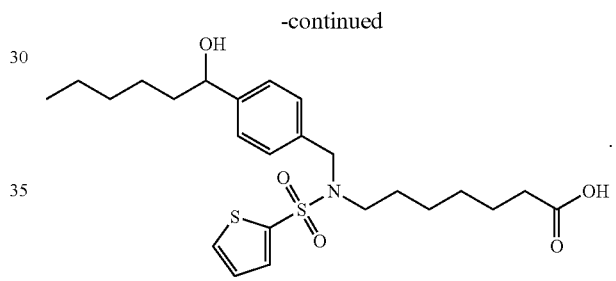 | 3.5 | 92 | 11 | 97 | 208 | 2 | NA | 89 | 1321 | EP3 = 1150<br>DP = 99 |
| (second structure) | 18<br>(5) | 87 | 20 | 93 | 100<br>(50) | 0 | NA | 59 | 1345<br>(>3200) | |

While particular embodiments of the invention have been described it will be understood of course that the invention is not limited thereto since many obvious modifications can be made and it is intended to include within this invention any such modifications as will fall within the scope of the appended claims.

The invention claimed is:

1. A novel compound having the formula selected from the group consisting of:

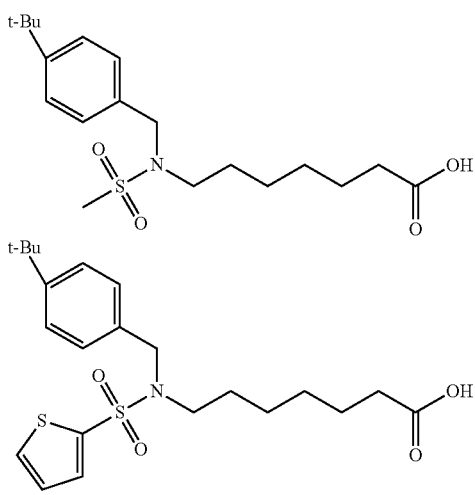

2. An ophthalmic solution comprising a therapeutically-effective amount of the compound of claim 1 in ophthalmically-acceptable vehicle.

3. The solution of claim 2 wherein said vehicle is saline.

4. The solution of claim 2 wherein said compound comprises from 0.001-5% w/v of said solution.

* * * * *